US005827826A

United States Patent [19]
Jaye et al.

[11] Patent Number: 5,827,826
[45] Date of Patent: *Oct. 27, 1998

[54] COMPOSITIONS OF HUMAN ENDOTHELIAL CELL GROWTH FACTOR

[75] Inventors: Michael Jaye, Glenside, Pa.; Wilson Burgess, Gaithersburg; Thomas Maciag, Rockville, both of Md.; William N. Drohan, Springfield, Va.

[73] Assignee: Rhone-Poulenc Rorer Pharmaceuticals Inc., Collegeville, Pa.

[ * ] Notice: The term of this patent shall not extend beyond the expiration date of Pat. No. 5,571,790.

[21] Appl. No.: 743,261

[22] Filed: Nov. 4, 1996

Related U.S. Application Data

[63] Continuation-in-part of Ser. No. 472,964, Jun. 7, 1995, Pat. No. 5,571,790, which is a continuation of Ser. No. 334,884, Nov. 3, 1994, Pat. No. 5,552,528, which is a continuation of Ser. No. 799,859, Nov. 27, 1991, abandoned, which is a continuation of Ser. No. 693,079, Apr. 29, 1991, abandoned, which is a continuation of Ser. No. 134,499, Dec. 18, 1987, abandoned, which is a continuation-in-part of Ser. No. 835,594, Mar. 3, 1986, Pat. No. 4,868,113.

[51] Int. Cl.⁶ ............................. A61K 38/18; C07K 14/50
[52] U.S. Cl. ............................ 514/12; 530/350; 530/399; 930/120
[58] Field of Search ..................... 514/2, 8, 12; 530/399; 930/120

[56] References Cited

U.S. PATENT DOCUMENTS

| | | |
|---|---|---|
| 4,394,443 | 7/1983 | Weissman et al. . |
| 4,401,662 | 8/1983 | Lormeau et al. . |
| 4,443,546 | 4/1984 | Stemerman et al. . |
| 4,444,760 | 4/1984 | Thomas . |
| 4,446,314 | 5/1984 | Jordan . |
| 4,468,464 | 8/1984 | Cohen et al. . |
| 4,612,367 | 9/1986 | Grinnan et al. . |
| 4,658,021 | 4/1987 | Goeddel et al. . |
| 4,668,476 | 5/1987 | Bridgham et al. . |
| 4,675,285 | 6/1987 | Clark et al. . |
| 4,696,917 | 9/1987 | Lindstrom et al. . |
| 4,788,135 | 11/1988 | Davis et al. . |
| 4,826,827 | 5/1989 | Lormeau et al. . |
| 4,882,275 | 11/1989 | Klagsbrun . |
| 5,032,679 | 7/1991 | Brandley et al. . |
| 5,348,941 | 9/1994 | Middaugh et al. . |
| 5,401,832 | 3/1995 | Linemeyer et al. . |
| 5,439,818 | 8/1995 | Fiddes et al. . |

FOREIGN PATENT DOCUMENTS

| | | |
|---|---|---|
| 437 281 | 4/1994 | European Pat. Off. . |
| WO 87/01728 | 3/1987 | WIPO . |

OTHER PUBLICATIONS

Lobb et al., Purification and Characterization of Heparin–binding Endothelial Cell Growth Factors, J. Biol. Chem., 264:4, 1924–1928 (1985).

Lobb et al., Comparison of Human and Bovine Brain Derived Heparin–Binding Growth Factors, Biochemical and Biophysical Research Communications, 131:2, 586–592 (1985).

Bohlen et al., Acidic fibroblast growth factor (FGF) from bovine brain: amino–terminal sequence and comparison with basic FGF, EMBO J., 4, 1951–1956 (1985).

Burgess et al., Multiple Forms of Endothelial Cell Growth Factor–Rapid Isolation and Biological and Chemical Characterization, J. Biol. Chem. 260, 11389–11392 (1985).

Collaborative Research Inc., Product Catalog (1983).

Collaborative Research Inc. Product Catalog (1986).

Conn et al., The Isolation and Purification of Two Anionic Endothelial Cell Growth Factors from Human Brain, Biochem. Biophys. Res. Comm. 124, 262–268 (1984).

de Ferra et al., Alternative splicing accounts for the four forms of myelin basic protein, Cell 43, 721–727 (1985).

Esch et al., Primary structure of bovine pituitary basic fibroblast growth factor (FGF) and comparison with the amino–terminal sequence of bovine brain acidic FGF, Proc. Natl. Acad. Sci., USA 82, 6507–6511 (1985).

Esch, Primary Structure of Bovine Brain Acidic Fibroblast Growth Factor ("FGF"), Biochem. Biophys. Res. Comm. 133, 554–562 (1985).

Gimenez–Gallego et al., Brain–Derived Acidic Fibroblast Growth Factor: Complete Amino acid Sequence and Homologies, Science, 230, 1385–1388 (1985).

Hunkapiller et al., High–sensitivity sequencing with a gas–phase sequenator, Meth. Enzymol. 91, 399–413 (1983).

Jaye et al., Isolation of a human–anti–haemophilic factor IX cDNA clone using a unique 52–base synthetic oligonucleotide probe deduced from the amino acid sequence of bovine factor IX, Nucl. Acids Res. 11, 2325–2335 (1983).

Jaye et al., Modulation of the sis Gene Transcript During Endothelial Cell Differentiation in Vitro, Science 228, 882–885 (1985).

Klagsbrun et al., Heparin affinity of anionic and cationic capillary endothelial cell growth factors: Analysis of hypothalamus–derived growth factors and fibroblast growth factors, Proc. Natl. Acad. Sci. USA 82, 805–809 (1985).

Lathe, Synthetic oligonucleotide probes deduced from amino acid sequence data: Theoretical and practical implications, J. Mol. Biol. 183, 1–12 (1985).

Lobb et al., Purification of two distinct growth factors from bovine neural tissue by heparin affinity chromatography, Biochemistry 23, 6295–6299 (1984).

Maciag, An endothelial cell growth factor from bovine hypothalamus: Identification and partial characterization, Proc. Natl. Acad. Sci., USA 76, 5674–5678 (1979).

(List continued on next page.)

*Primary Examiner*—John Ulm
*Assistant Examiner*—Christine Saoud

[57] ABSTRACT

The present invention is directed to compositions comprising endothelial cell growth factor, an acceptable carrier and, optionally, an extracellular matrix protein, a glycosaminoglycan or serum albumin. The compositions are useful for wound repair.

10 Claims, 12 Drawing Sheets

OTHER PUBLICATIONS

Maciag, High and Low Molecular Weight Forms of Endothelial Cell Growth Factor, J. Biol. Chem. 257, 5333–5336 (1982).

Maciag, Angiogenesis, Prog. Hemo. Thromb. 7, 167–182 (1984).

Maciag, Heparin binds endothelial cell growth factor, the principal endothelial cell mitogen in bovine brain, Science 225, 932–935 (1984).

Maciag et al., Preparation of endothelial cell growth factor, Cell Cult. Methods, Mol. Cell. Biol. 1, 195–205 (1984).

Marglin et al., Chemical synthesis of peptides and proteins, Ann. Rev. Biochem. 39, 841–866 (1970).

Metzler, , Biochemistry, Academic Press, Inc. London 901 (1977).

Schreiber et al., Interaction of endothelial cell growth factor with heparin: Characterization by receptor and antibody recognition, Proc. Natl. Acad. Sci. USA 82, 6138–6142 (1985).

Schreiber et al., A unique family of endothelial cell mitogens: The antigenic receptor cross–reactivity of bovine endothelial cell growth factor, brain–derived acidic fibroblast growth factor, and eye–derived growth factor–II, J. Cell. Biol. 101, 1623–1626 (1985).

Thomas, Purification and characterization of acidic fibroblast growth factor from bovine brain, Proc. Natl. Acad. Sci. USA 81, 357–361 (1984).

Thomas et al., Pure brain–derived acidic fibroblast growth factor is a potent angiogenic vascular endothelial cell mitogen with sequence homology to interleukin 1, Proc. Natl. Acad. Sci. USA 82, 6409–6413 (1985).

Thomas et al., Fibroblast growth factors: broad spectrum mitogens with potent angiogenic activity, Trends in Biochem Sci. 11, 81–84 (1986).

Watson, Recombination at the Molecular Level, Molecular Biology of the Gene (1987).

Webster's II Riverside Univ. Dictionary, p. 444 (1984).

Mestre et al., Comparative Effects of Heparin and PK 10169, A Low Molecular Weight Fraction, In a Canine Model of Arterial Thrombosis, Thrombosis Research, 38, 389–399 (1985).

Alberts et al., The Extracellular Matrix, Molecular Biology of the Cell, Garland Pub., 692–715 (1983).

FIG.3 a.     (H₂N)-AsnTyrLysLysPro  
                                                 5 b.     AcAlaGluGlyGluThrThrThrPheThrAlaLeuThrGluLysPheAsnLeuProLeuGlyAsnTyrLysLysPro 10                 15                20                25                30 a.     LysLeuLeuTyrCysSerAsnGlyGlyTyrPheLeuArgIleLeuProAspGlyThrValAspGlyThrLysAspHis...

b.     LysLeuLeuTyrCysSerAsnGlyGlyTyrPheLeuArgIleLeuProAspGlyThrValAspGlyThrLysAspHis...

c.     AspThrAspGluLeuLeuTyrGlyGlySerGlnThrProAsnGluGlu d.     AspThrAspGluLeuLeuTyrGlyGlySerGlnThrProAsnGluGlu

Hydrogen-Bonded Base Pairs
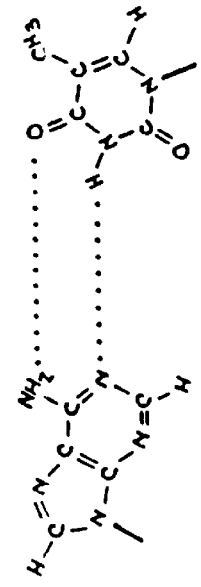
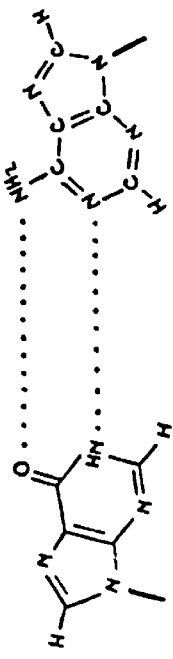
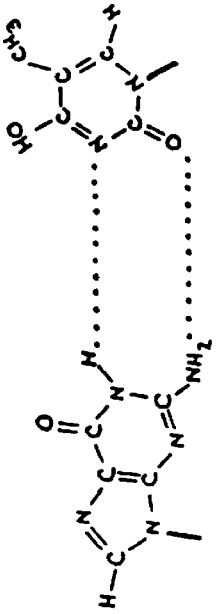
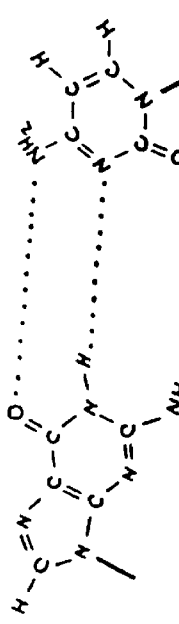
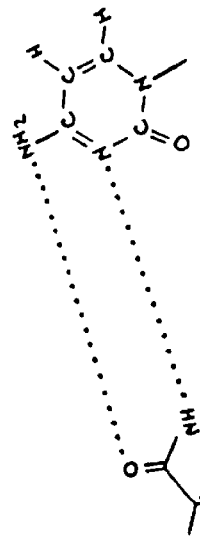
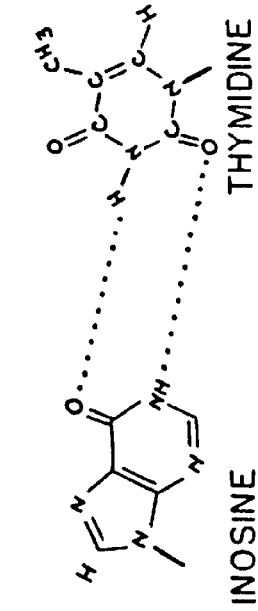
FIG. 4

DESIGN OF AN OLIGONUCLEOTIDE PROBE FOR

HUMAN ENDOTHELIAL CELL GROWTH FACTOR bovine ECGF
protein sequence:       I    L    P    D    G    T    V    D    G    T    K degenerate coding
sequence:          $AT_T^A$ CTX CCX $GA_T^C$ GGX ACX GTX $GA_T^C$ GGX ACX $AA_G^A$
                     C $TT_G^A$ $3 \times 6 \times 4 \times 2 \times 4 \times 4 \times 4 \times 2 \times 4 \times 2 \times 2 = 2.95 \times 10^5$ $AT_T^A$ CTX CCX $GA_T^C$ GGX ACX GTX $GA_T^C$ GGX ACX $AA_G^A$
                     C $TT_G^A$ CG dinucleotide:      not C or G          not C              not G
                                          or G
                              not C              not C C
                        G
                   $AT_T^A$ $C_T^A$$T_T$ $CC_T^A$ GAT GGX $AC_T^A$ GTX $GA_T^C$ GGX ACX $AA_G^A$
                        C       T $3 \times 8 \times 2 \times 1 \times 4 \times 2 \times 4 \times 2 \times 4 \times 4 \times 2 = 9.84 \times 10^4$ codon usage:       ATT $^C_T$TT $CC_T^A$ GAT GGX $AC_T^A$ GTX GAT GGX $AC_T^A$ AAA
                                                                     C
                   $1 \times 2 \times 2 \times 1 \times 4 \times 2 \times 4 \times 1 \times 4 \times 3 \times 1 = 1.54 \times 10^3$ allowance for
inosine and
G:T basepairs:     ATT TTT CCI GAT GGI ACI GTI GAT GGI ACI AAA 16 A/T
                                                              11 G/C
                                                               6 I
                                                              ———
                           FIG.5                               33

HOMOLOGY BETWEEN HUMAN ECGF cDNA SEQUENCE AND OLIGONUCLEOTIDE PROBES

```
a.        F   N   L   P   L   G   N   Y   K   K   P   K   L   L   Y   C   S   N   G   G   Y   F   L   R     I   L   P   D   G   T   V   D   G   T   K
b.                                AACTACAAAAACCIAAACTICTITACTGCTCIAACGGIGGITACTTC         ATTTTTCCIGATGGIACIGTIGATGGIACIAAA
          ::  ::  ::  ::  ::  :: ::: ::  ::  ::::: ::  :::::: /:: /:::::                 ::://:::::/:::::  ::/::/::://::/:
c.      TTTAATCTGCCTCCAGGGAATTACAAGAAGCCCAAACTCCTCTACTGTAGCAATGGGGGCCACTTCCTGAGGATCCTTCCGAGATGGCACAGTGGATGGGACAAGG
d.        F   N   L   P   L   G   N   Y   K   K   P   K   L   L   Y   C   S   N   G   G   Y   F   L   R     I   L   P   D   G   T   V   D   G   T   K
                                                  ECGF Oligonucleotide II*                                      ECGF Oligonucleotide I a.        M   D   T   D   G   L   L   Y   G   S   Q   T   P   N   E   E
b.      ATGGACACIGACGGICTICTICTTTACGGITCICAGACACICCIAACGAGGAG
        ::::::: ::::/::/ :/:::: ::/::::: ::/::/::/::::/
c.      ATGGACACCGACGGGCTTTTATACGGCTCACAGACACCAAATGAGGAA
d.        M   D   T   D   G   L   L   Y   G   S   Q   T   P   N   E   E
                            ECGF Oligonucleotide III*
``` a. Bovine ECGF protein sequence
b. Oligonucleotide probe
c. Human ECGF cDNA sequence
d. Human ECGF deduced amino acid sequence
: Signifies G:C or A:T base pairing
/ Signifies unusual base pairing
* Actual oligonucleotide used was the complement of the sequence shown

COMPOSITIONS OF HUMAN ENDOTHELIAL CELL GROWTH FACTOR

CROSS-REFERENCE TO RELATED APPLICATIONS

This application is a continuation-in-part of application Ser. No. 08/472,964, filed Jun. 7, 1995, now U.S. Pat. No. 5,571,790, which is a continuation of application Ser. No. 08/334,884, filed Nov. 3, 1994, now U.S. Pat. No. 5,552,528, which is a continuation of application Ser. No. 07/799,859, filed Nov. 27, 1991, now abandoned, which is a continuation of application Ser. No. 07/693,079, filed Apr. 29, 1991, now abandoned, which is a continuation of application Ser. No. 07/134,499, filed Dec. 18, 1987,now abandoned, which is a continuation-in-part of application Ser. No. 06/835,594, filed Mar. 3, 1986, now U.S. Pat. No. 4,868,113.

BACKGROUND OF THE INVENTION

(1) Field of the Invention

This invention relates to recombinant DNA-directed synthesis of certain proteins. More particularly, this invention relates to endothelial cell growth factor (ECGF), its recombinant DNA-directed synthesis, and ECGF's use in the treatment of endothelial cell damage and/or regeneration.

(2) The Prior Art

Endothelial cell growth factor, referred to herein as "ECGF", is a mitogen for endothelial cells in vitro. Growth of endothelial cells is a necessary step during the process of angiogenesis [Maciag, *Prog. Hemostasis and Thromb.,* 7:167–182 (1984); Maciag, T., Hoover, G. A., and Weinstein, R., *J. Biol. Chem.,* 257: 5333–5336 (1982)]. Bovine ECGF has been isolated by Maciag, et al., [*Science* 225:932–935 (1984)] using streptomycin sulfate precipitation, gel exclusion chromatography, ammonium sulfate precipitation and heparin-Sepharose affinity chromatography. Bovine ECGF purified in this manner yields a single-chain polypeptide which possesses an anionic isoelectric point and an apparent molecular weight of 20,000 [Maciag, supra; Schreiber, et al., *J. Cell Biol.,* 101:1623–1626 (1985); and Schreiber, et al., *Proc. Natl. Acad. Sci.,* 82:6138–6142 (1985)]. More recently, multiple forms of bovine ECGF have been isolated by Burgess, et al., [*J. Biol. Chem.* 260:11389–11392 (1985)] by sodium chloride gradient elution of bovine ECGF from the heparin-Sepharose column or by reversed-phase high pressure liquid chromatography (HPLC). The two isolated polypeptides, designated alpha- and beta-ECGF have apparent molecular weights of 17,000 and 20,000, respectively. Using this procedure, the bovine ECGF contained in 8,500 ml of bovine brain extract ($6.25 \times 10^7$ total units) is concentrated into a total of 6 ml of alpha-ECGF ($3.0 \times 10^6$ units) and 3 ml of beta-ECGF ($5.2 \times 10^5$ units). This is a 9,300-fold purification of alpha-ECGF and 16,300-fold purification of beta-ECGF (Burgess, supra.). Recently, murine monoclonal antibodies against bovine ECGF have been produced (Maciag, et al., supra.) which may be useful in purifying bovine ECGF in a manner similar to the monoclonal antibody purification of Factor VIIIC described by Zimmerman and Fulcher in U.S. Pat. No. 4,361,509.

In general, recombinant DNA techniques are known. See *Methods In Enzymology,* (Academic Press, New York) volumes 65 and 68 (1979); 100 and 101 (1983) and the references cited therein, all of which are incorporated herein by reference. An extensive technical discussion embodying most commonly used recombinant DNA methodologies can be found in Maniatis, et al., *Molecular Cloning,* Cold Spring Harbor Laboratory (1982). Genes coding for various polypeptides may be cloned by incorporating a DNA fragment coding for the polypeptide in a recombinant DNA vehicle, e.g., bacterial or viral vectors, and transforming a suitable host. This hose is typically an *Escherichia coli* (*E. coli*) strain, however, depending upon the desired product, eukaryotic hosts may be utilized. Clones incorporating the recombinant vectors are isolated and may be grown and used to produce the desired polypeptide on a large scale.

Several groups of workers have isolated mixtures of messenger RNA (mRNA) from eukaryotic cells and employed a series of enzymatic reactions to synthesize doublestranded DNA copies which are complementary to this mRNA mixture. In the first reaction, mRNA is transcribed into a singlestranded complementary DNA (cDNA) by an RNA-directed DNA polymerase, also called reverse transcriptase. Reverse transcriptase synthesizes DNA in the 5'-3' direction, utilizes deoxyribonucleoside 5'-triphosphates as precursors, and requires both a template and a primer strand, the latter of which must have a free 3'-hydroxyl terminus. Reverse transcriptase products, whether partial or complete copies of the mRNA template, often possess short, partially double-stranded hairpins ("loops") at their 3' termini. In the second reaction, these "hairpin loops" can be exploited as primers for DNA polymerases. Preformed DNA is required both as a template and as a primer in the action of DNA polymerase. The DNA polymerase requires the presence of a DNA strand having a free 3'-hydroxyl group, to which new nucleotides are added to extend the chain in the 5'-3' direction. The products of such sequential reverse transcriptase and DNA polymerase reactions still possess a loop at one end. The apex of the loop or "fold-point" of the double-stranded DNA, which has thus been created, is substantially a single-strand segment. In the third reaction, this single-strand segment is cleaved with the single-strand specific nuclease S1 to generate a "blunt-end" duplex DNA segment. This general method is applicable to any mRNA mixture, and is described by Buell, et al., *J. Biol. Chem.,* 253:2483 (1978).

The resulting double-stranded cDNA mixture (ds-cDNA) is inserted into cloning vehicles by any one of many known techniques, depending at least in part on the particular vehicle used. Various insertion methods are discussed in considerable detail; in *Methods In Enzymology,* 68:16–18 (1980), and the references cited therein.

Once the DNA segments are inserted, the cloning vehicle is used to transform a suitable host. These cloning vehicles usually impart an antibiotic resistance trait on the host. Such hosts are generally prokaryotic cells. At this point, only a few of the transformed or transfected hosts contain the desired cDNA The sum of all transformed or transfected hosts constitutes a gene "library". The overall ds-cDNA library created by this method provides a representative sample of the coding information present in the mRNA mixture used as the starting material.

If an appropriate oligonucleotide sequence is available, it can be used to identify clones of interest in the following manner. Individual transformed or transfected cells are grown as colonies on a nitrocellulose filter paper. These colonies are lysed; the DNA released is bound tightly to the filter paper by heating. The filter paper is then incubated with a labeled oligonucleotide probe which is complementary to the structural gene of interest. The probe hybridizes with the cDNA for which it is complementary, and is identified by autoradiography. The corresponding clones are characterized in order to identify one or a combination of clones which contain all of the structural information for the desired protein. The nucleic acid sequence coding for the protein of interest is isolated and reinserted into an expression vector. The expression vector brings the cloned gene under the regulatory control of specific prokaryotic or eukaryotic control elements which allow the efficient expression (transcription and translation) of the ds-cDNA. Thus, this general technique is only applicable to those proteins for which at least a portion of their amino acid or DNA sequence is known for which an oligonucleotide probe is available. See, generally, Maniatis, et al., supra.

More recently, methods have been developed to identify specific clones by probing bacterial colonies or phage plaques with antibodies specific for the encoded protein of interest. This method can only be used with "expression vector" cloning vehicles since elaboration of the protein product is required. The structural gene is inserted into the vector adjacent to regulatory gene sequences that control expression of the protein. The cells are lysed, either by chemical methods or by a function supplied by the host cell or vector, and the protein is detected by a specific antibody and a detection system such as enzyme immunoassay. An example of this is the lambda gtll system described by Young and Davis, *Proc. Nat'l. Acad. Sci. USA,* 80:1194–1198 (1983) and Young and Davis, *Science,* 222:778 (1983).

SUMMARY OF THE INVENTION

The present invention has made it possible to provide readily available, large quantities of ECGF or ECGF fragments. This has been achieved with oligonucleotides whose design was based upon knowledge of the amino acid sequence of bovine ECGF and which react specifically with the ECGF cDNA. Production of ECGF is achieved through the application of recombinant DNA technology to prepare cloning vehicles encoding the ECGF protein and procedures for recovering ECGF protein essentially free of other proteins of human origin.

Accordingly, the present invention provides ECGF or its fragments essentially free of other proteins of human origin. ECGF is produced by recombinant DNA techniques in host cells or other self-replicating systems and is provided in essentially pure form. The invention further provides replicable expression vectors incorporating a DNA sequence encoding ECGF and a self-replicating host cell system transformed or transfected thereby. The host system is usually of prokaryotic, e.g., *E. coli* or *B. subtilis,* or eukaryotic cells.

The ECGF is produced by a process which comprises (a) preparing a replicable expression vector capable of expressing the DNA sequence encoding ECGF in a suitable host cell system; (b) transforming said host system to obtain a recombinant host system; (c) maintaining said recombinant host system under conditions permitting expression of said ECGF-encoding DNA sequence to produce ECGF protein; and (d) recovering said ECGF protein. Preferably, the ECGF-encoding replicable expression vector is made by preparing a ds-cDNA preparation representative of ECGF mRNA and incorporating the ds-cDNA into replicable expression vectors. The preferred mode of recovering ECGF comprises reacting the proteins expressed by the recombinant host system with a reagent composition comprising at least one binding step specific for ECGF. ECGF may be used as a therapeutic agent in the treatment of damaged or in regenerating blood vessels and other endothelial cell-lined structures.

BRIEF DESCRIPTION OF THE DRAWINGS

FIG. 3 illustrates a partial amino acid sequence of bovine alpha and beta ECGF.

Line a: Amino-terminal amino acid sequence of bovine alpha ECGF.

Line b: Amino-terminal amino acid sequence of bovine beta ECGF. The portion in parenthesis corresponds to NH2-terminal segment for which sequence could not be determined; amino acid composition is shown instead. The sequence beginning with PheAsnLeu . . . was determined from trypsin-cleaved bovine beta ECGF.

Line c: Amino acid sequence of cyanogen bromide-cleaved bovine alpha ECGF.

Line d: Amino acid sequence of cyanogen bromide-cleaved bovine beta ECGF.

FIG. 4 illustrates hydrogen-bonded base pairs.

FIG. 5 illustrates the design of an oligonucleotide probe for human Endothelial Cell Growth Factor.

Figure 6:
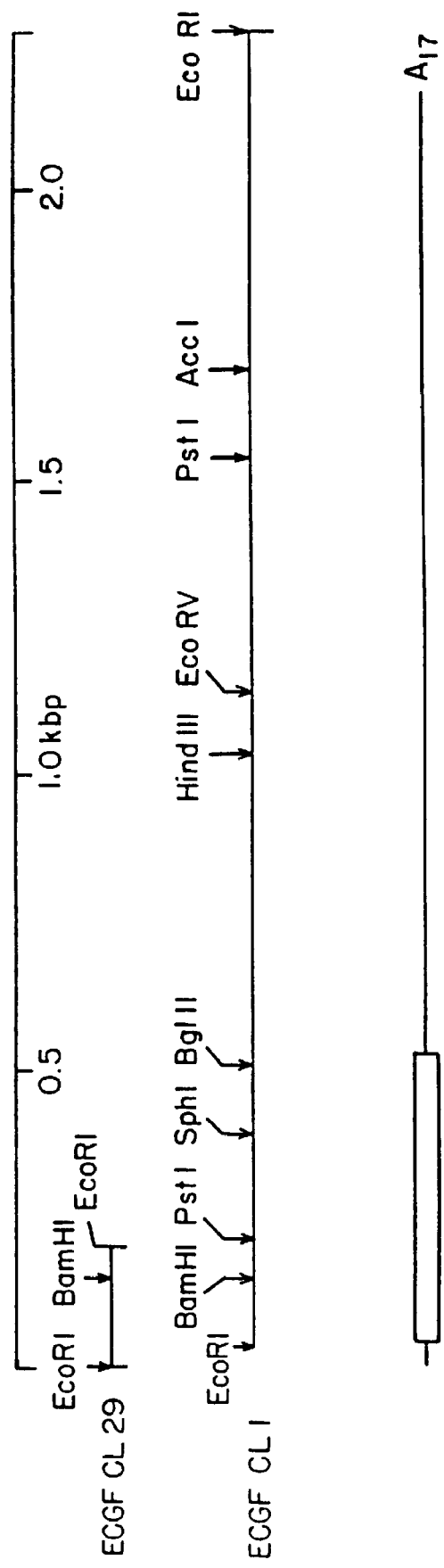

FIG. 6 illustrates a schematic diagram of human ECGF cDNA clones 1 and 29. The open reading box represents the open reading frame encoding human beta ECGF. The EcoRI sites correspond to synthetic oligonucleotide linkers used in the construction of the cDNA library. The poly (A) tail at the 3' end of clone 1 is shown by A17.

FIG. 7 illustrates homology between human ECGF cDNA sequence and oligonucleotide probes.

Line a: Bovine trypsin- or cyanogen bromide-cleaved beta ECGF amino acid sequence.

Line b: Unique oligonucleotide probe.

Line c: Human ECGF cDNA sequence (determined from lambda ECGF clones 1 and 29).

Line d: Human ECGF amino acid sequence, deduced from cDNA sequence analysis.

Figure 8:
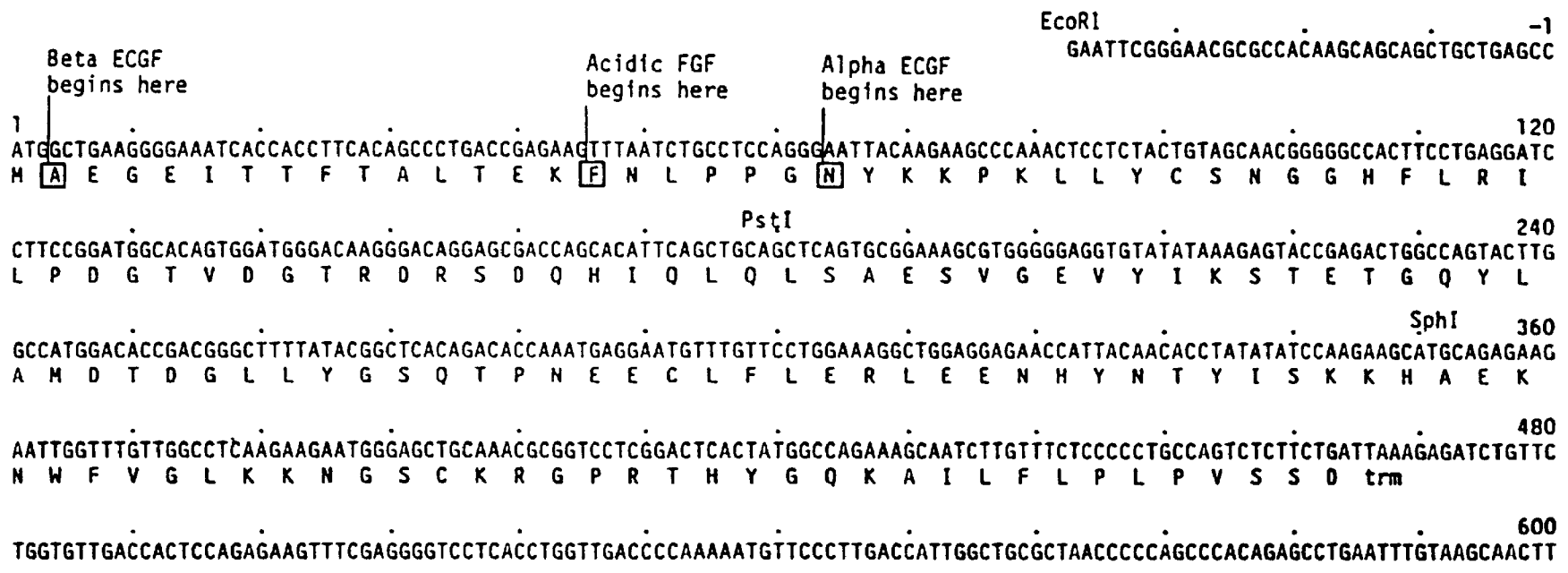

FIG. 8 illustrates the complete cDNA sequence of human ECGF. The cDNA inserts from ECGF clones 1 and 29 were subcloned into M13mp18 and the ECGF-encoding open reading frame and flanking regions sequenced by the chain termination method. In frame stop codons at the 5' and 3' ends of the ECGF-encoding open reading frame are indicated by the underlined sequence and trm, respectively. The single-letter notation for amino acids is used: A, Ala; C, Cys; D, Asp; E, Glu; F. Phe; G. Gly; H. His; I, Ile; K, Lys; L, Leu; M, Met; N. Asn; P. Pro; Q. Gln; R. Arg; S. Ser; T. Thr; V, Val; W. Trp; Y. Tyr.

Figure 9:
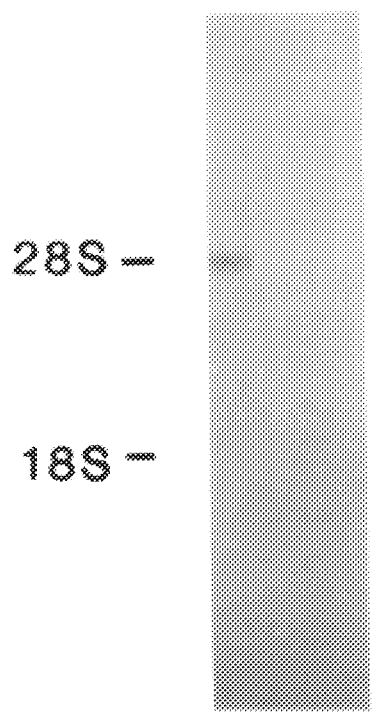

FIG. 9 illustrates Northern blot analysis of ECGF mRNA. RNA was denatured in 2.2M formaldehyde and 50% formamide and fractionated by electrophoresis in a 1.25% agarose gel containing 2.2M formaldehyde. This was transferred to GeneScreen Plus (New England Nuclear) by blotting with 10X SSPE. Blots were hybridized to $^{32}$p-labeled nick-translated probes of ECGF clone 1 at 65° C. for 16 hours in a mixture containing 2X SSPE, 20X Denhardt's solution, yeast transfer RNA (200 µg/ml), and 0.2% SDS. The membrane was subsequently washed at 65° C., twice with 2X SSPE and 0.2% SDS, then twice with 0.2X SSPE and 0.2% SDS, air-dried, and exposed overnight to Kodak XAR film with an intensifying screen. The migration of 28S and 18S RNA is noted. Lane 1: 10 µg human brain poly(A)-containing RNA. Lane 2: 10 µg human adult liver poly(A)-containing RNA.

Figure 10:
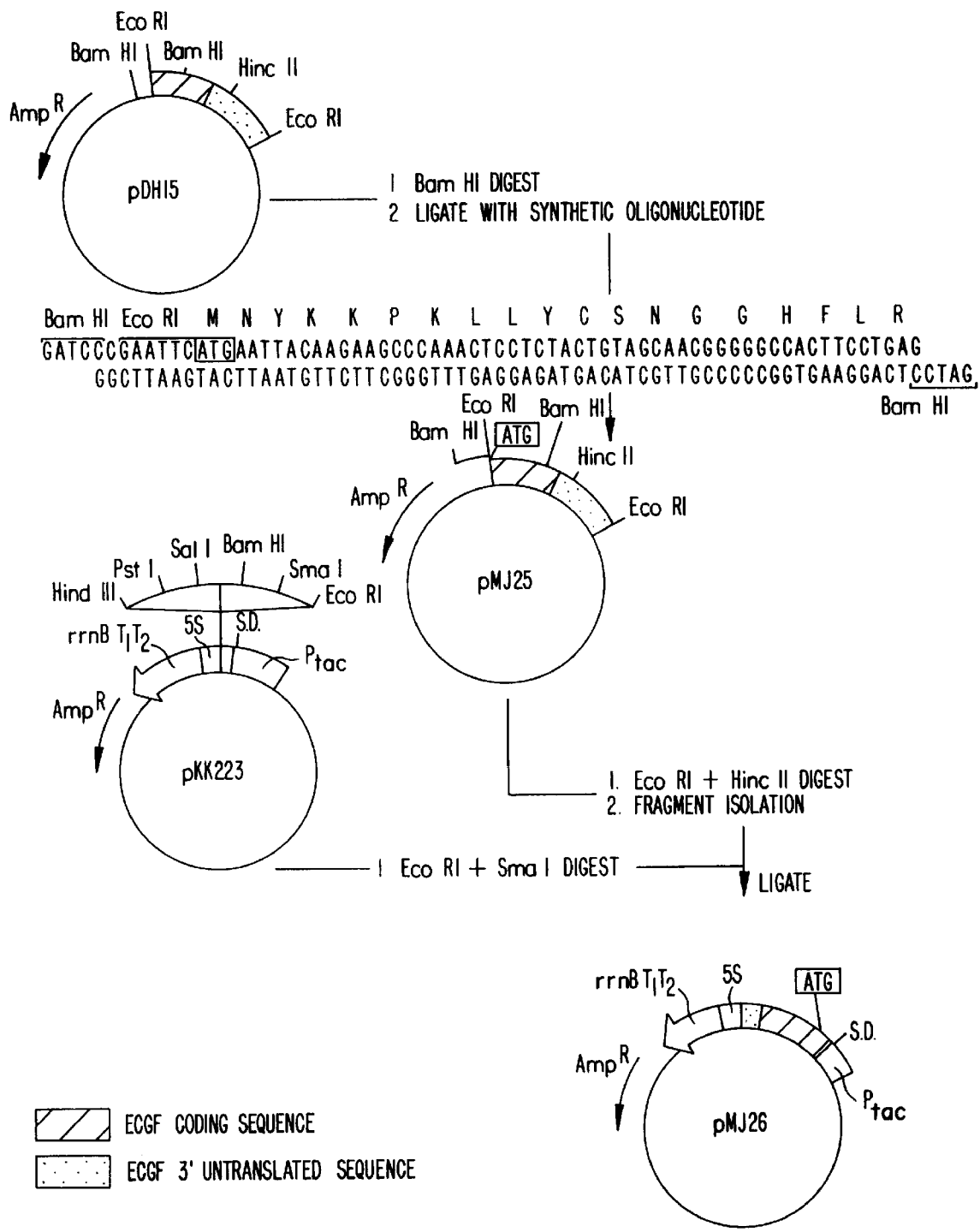

FIG. 10 illustrates expressional cloning of human recombinant α-ECGF. The expression vector pMJ26 was constructed as indicated. The translation initiation codon provided by the synthetic oligonucleotide is indicated by "ATG". The hybrid tac promoter and the Shine-Dalgarno sequence provided by the vector pKK223-3, are indicated by "Ptac" and S.D.", respectively. Transcription terminators are indicated by "rrnBT$_1$T$_2$" and "5S". The open arrow shows the direction of transcription from the tac promoter.

Figure 11:
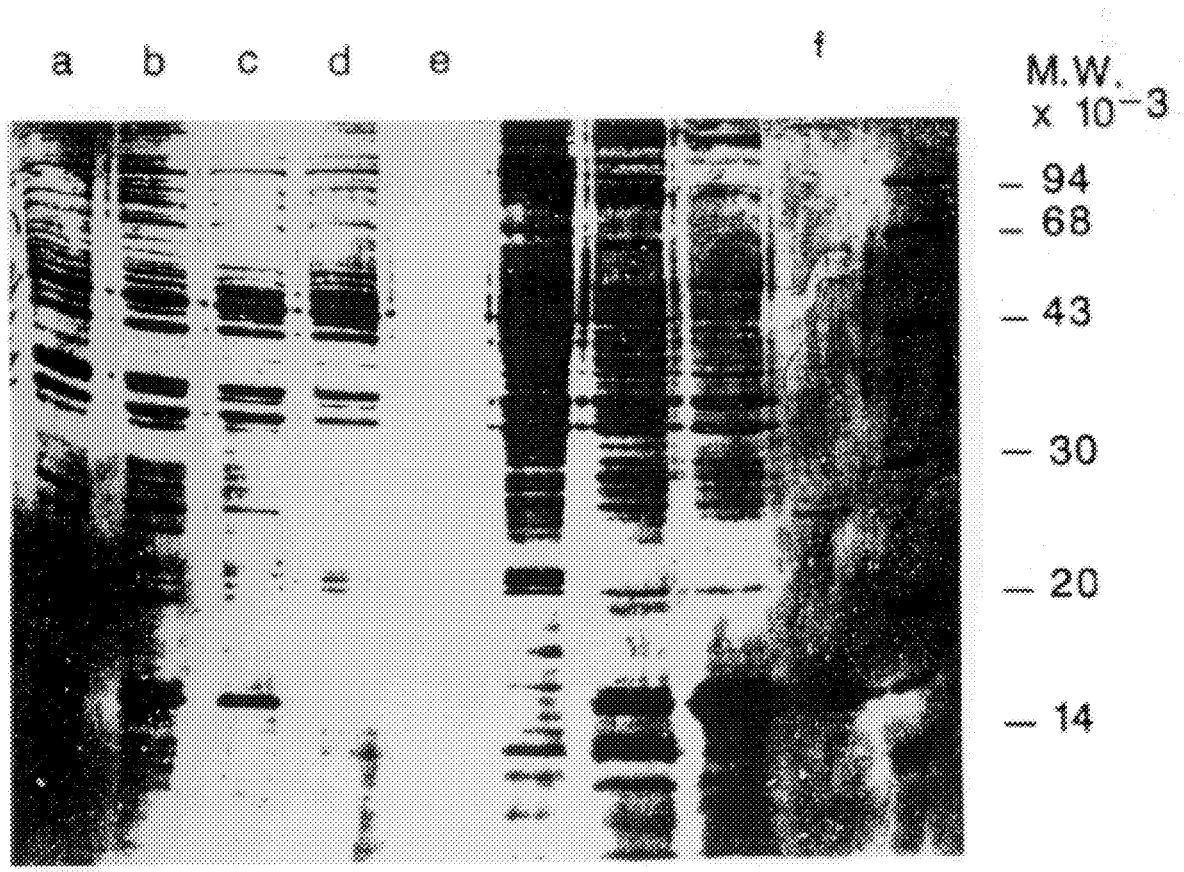

FIG. 11 illustrates SDS-PAGE analysis of recombinant human α-ECGF expression and purification. Cultures of pMJ26 in *E. coli* JM103 were grown and induced with 1 mM IPTG. Lanes a and b, samples lysed in Laemmli sample buffer. Lane a, uninduced pMJ26. Lane b, induced pMJ26. Lanes c–f, purification of ECGF from induced pMJ26. Lane c, supernatant, after removal of cell debris; Lane d, material unabsorbed to heparin-Sepharose in 250 mM NaCl; lane e, entire cell debris pellet of lane c; Lane f, molecular weight standards. Samples in lanes a–d contained 100 μg protein.

FIG. 12 illustrates a comparison of human recombinant and bovine brain-derived α-ECGF. ──○──○──○── bovine α-ECGF; ──●──●──●── recombinant human α-ECGF; ──□──□──□── reduced and alkylated recombinant human α-ECGF; ■ recombinant human α-ECGF, no heparin; □ bovine α-ECGF, no heparin.

Figure 12A:
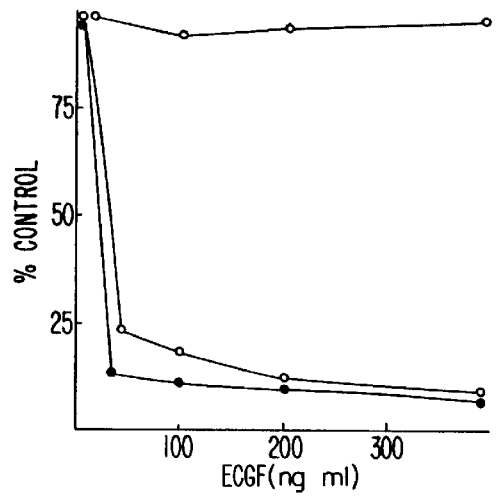

FIG. 12A. Le-II receptor binding competition assay. Receptor competition assays were performed. Confluent cultures of LE-II cells were incubated for 1.5 h at 4° C. in the present of approximately 5 ng/ml of $^{25}$I-bovine α-ECGF and the indicated amounts of unlabelled HPLC-purified α-ECGF. Protein concentrations were determined by amino acid analysis. Monolayers were washed three times with DMEM containing 1 mg/ml BSA, lysed with 0.1N NaOH, and the cell-associated radioactivity determined. Binding observed in the absence of competitor is defined as 100% control. Reduced and alkylated recombinant α-ECFG was prepared as follows: HPLC-purified ECGF in Tris-HCl pH 8.3, 6M guanidine hydrochloride, 100 mM DTT was incubated for 60 minutes at 37° C. under nitrogen. Iodacetic acid was added to 22 mM, and incubation continued in the dark for 60 minutes at 37° C. The protein was isolated by reversed-phase HPLC. Amino acid composition analysis indicated the presence of 2.9 mol s-carboxymethyl cystein, mol α-ECGF.

Figure 12B:
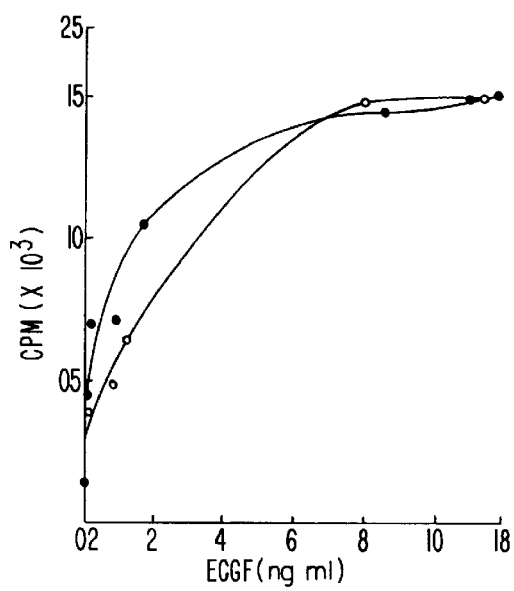

FIG. 12B. Stimulation of [$^3$H]-thymidine incorporation in LE-II cells. Confluent, murine LE-II cells in DMEM containing 0.1% fetal bovine serum were incubated with the indicated quantities of bovine or recombinant human α-ECGF for 18 hours. Cells were labelled for 4 hours in the presence of 2.4 uCi [$^3$H]-thymidine. Wells containing 20% fetal calf serum (X) and 1 mg/ml bovine serum albumin (BSA) served as controls.

Figure 12C:
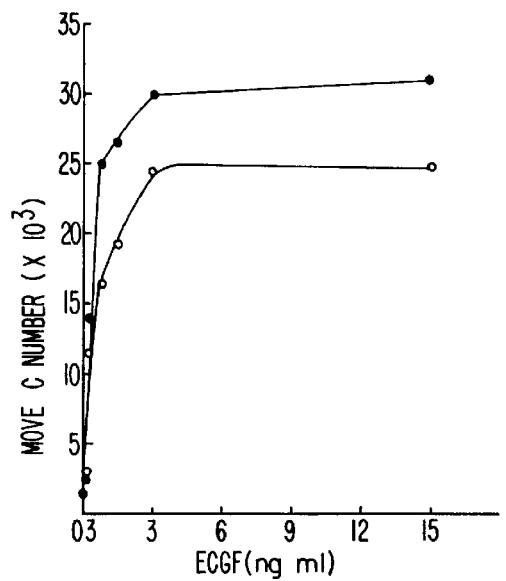

FIG. 12C. Human umbilical vein endothelial cell (HUVEC) growth assay. Costar 24 well tissue culture dishes (2 cm$^2$/well) were precoated with human fibronectin (10 μg/cm$^2$) in PBS for 0.5–2 hours prior to seeding with 2×10$^3$ HUVEC in Medium 199 containing 10% fetal bovine serum. Cells were allowed to attach for 2–4 hours at 37° C., at which time the media was aspirated and replaced with 0.75 ml Medium 199 containing 10% fetal bovine serum and, unless otherwise indicated, 5 U/ml heparin. Dilutions of HPLC-purified recombinant human α-ECGF and bovine brain-derived α-ECGF in 1–50 μl were added to duplicate wells as indicated. Media were changed on days 2 and 4, and on day 7 cells were harvested by trypsinization and cell number was determined with a Coulter counter. Wells containing 20% fetal calf serum (X) and 1 ng/ml BSA served as controls.

DESCRIPTION OF THE PREFERRED EMBODIMENTS

A. Introduction

As used herein, "ECGF" denotes endothelial cell growth factor or its fragments produced by cell or cell-free culture systems, in bioactive forms having the capacity to influence cellular growth, differentiation, and migration in vitro as does ECGF native to the human angiogenic process.

Different alleles of ECGF may exist in nature. These variations may be characterized by differences in the nucleotide sequence of the structural gene coding for proteins of identical biological function. It is possible to produce analogs having single or multiple amino acid substitutions, deletions, additions, or replacements. All such allelic variations, modifications, and analogs resulting in derivatives of ECGF which retain the biologically active properties of native ECGF are included within the scope of this invention.

The glycosaminoglycan heparin potentiates the mitogenic effect of both bovine and recombinant human ECGF. Heparin naturally exists as a heterogeneous mixture of polysaccharide chains ranging from about 6,000 to about 25,000 Da (Alberts et al. in "Molecular Biology of the Cell" Garland Publishing, Inc. (1983) pp. 692–715). Low molecular weight heparins (LMWH) having a variety of advantages over natural heparin have been prepared (see U.S. Pat. Nos. 4,401,662; 4,446,314; 4,826,827; 5,032,679 and Mestre et al. Thrombosis Research 38, 389–399 (1985)) and are also useful in the practice of the present invention.

"Expression vectors" refer to vectors which are capable of transcribing and translating DNA sequences contained therein, where such sequences are linked to other regulatory sequences capable of affecting their expression. These expression vectors must be replicable in the host organisms or systems either as episomes, bacteriophage, or as an integral part of the chromosomal DNA. One form of expression vector which is particularly suitable for use in the invention is the bacteriophage, viruses which normally inhabit and replicate in bacteria. Particularly desirable phage for this purpose are the lambda gt$_{10}$ and gt$_{11}$ phage described by Young and Davis, supra. Lambda gtll is a general recombinant DNA expression vector capable of producing polypeptides specified by the inserted DNA.

To minimize degradation, upon induction with a synthetic analogue of lactose (IPTG), foreign proteins or portions thereof are synthesized fused to the prokaryotic protein B-galactosidase. The use of host cells defective in protein degradation pathways may also increase the lifetime of novel proteins produced from the induced lambda gt$_{11}$ clones. Proper expression of foreign DNA in lambda gt$_{11}$ clones will depend upon the proper orientation and reading frame of the inserted DNA with respect to the B-galactosidase promoter and translation initiating codon.

Another form of expression vector useful in recombinant DNA techniques is the plasmid—a circular unintegrated (extra-chromosomal), double-stranded DNA loop. Any other form of expression vector which serves an equivalent function is suitable for use in the process of this invention.

Recombinant vectors and methodology disclosed herein are suitable for use in host cells covering a wide range of prokaryotic and eukaryotic organisms. Prokaryotic cells are preferred for the cloning of DNA sequences and in the construction of vectors. For example, *E. coli* K12 strain HB101 (ATCC No. 33694), is particularly useful. Of course, other microbial strains may be used. Vectors containing replication and control sequences which are derived from species compatible with the host cell or system are used in connection with these hosts. The vector ordinarily carries an origin of replication, as well as characteristics capable of providing phenotypic selection in transformed cells. For example, *E. coli* can be transformed using the vector pBR322, which contains genes for ampicillin and tetracycline resistance [Bolivar, et al., *Gene,* 2:95 (1977)].

These antibiotic resistance genes provide a means of identifying transformed cells. The expression vector may also contain control elements which can be used for the expression of the gene of interest. Common prokaryotic control elements used for expression of foreign DNA sequences in *E. coli* include the promoters and regulatory sequences derived from the β-galactosidase and tryptophan (trp) operons of *E. coli,* as well as the pR and pL promoters of bacteriophage lambda. Combinations of these elements have also been used (e.g., TAC, which is a fusion of the trp promoter with the lactose operator). Other promoters have also been discovered and utilized, and details concerning their nucleotide sequences have been published enabling a skilled worker to combine and exploit them functionally.

In addition to prokaryotes, eukaryotic microbes, such as yeast cultures, may also be used. *Saccharomyces cerevisiae,* or common baker's yeast, is the most commonly used among eukaryotic microorganisms, although a number of other strains are commonly available. Yeast promoters suitable for the expression of foreign DNA sequences in yeast include the promoters for 3-phosphoglycerate kinase or other glycolytic enzymes. Suitable expression vectors may contain termination signals which provide for the polyadenylation and termination of the mRNA transcript of the cloned gene. Any vector containing a yeast-compatible promoter, origin of replication, and appropriate termination sequence is suitable for expression of ECGF.

Cell lines derived from multicellular organisms may also be used as hosts. In principle, any such cell culture is workable, whether from a vertebrate or invertebrate source. However, interest has been greatest in vertebrate cells, and propagation of vertebrate cells in culture (tissue culture) has become a routine procedure in recent years. Examples of such useful hosts are the VERO, HeLa, mouse C127, Chinese hamster ovary (CHO), W138, BHK, COS-7, and MDCK cell lines. Expression vectors for such cells ordinarily include an origin of replication, a promoter located in front of the gene to be expressed, RNA splice sites (if necessary), and transcriptional termination sequences.

For use in mammalian cells, the control functions (promoters and enhancers) on the expression vectors are often provided by viral material. For example, commonly used promoters are derived from polyoma, Adenovirus 2, and most frequently, Simian Virus 40 (SV40). Eukaryotic promoters, such as the promoter of the murine metallothionein gene [Paulakis and Hamer, *Proc. Natl. Acad. Sci.* 80:397–401 (1983)], may also be used. Further, it is also possible, and often desirable, to utilize the promoter or control sequences which are naturally associated with the desired gene sequence, provided such control sequences are compatible with the host system. To increase the rate of transcription, eukaryotic enhancer sequences can also be added to the construction. These sequences can be obtained from a variety of animal cells or oncogenic retroviruses such as the mouse sarcoma virus.

An origin of replication may be provided either by construction of the vector to include an exogenous origin, such as that provided by SV40 or other viral sources, or may be provided by the host cell chromosomal replication mechanism. If the vector is integrated into the host cell chromosome, the latter is often sufficient.

Host cells can prepare ECGF which can be of a variety of chemical compositions. The protein is produced having methionine as its first amino acid. This methionine is present by virtue of the ATG start codon naturally existing at the origin of the structural gene or by being engineered before a segment of the structural gene. The protein may also be intracellularly or extracellularly cleaved, giving rise to the amino acid which is found naturally at the amino terminus of the protein. The protein may be produced together with either its own or a heterologous signal peptide, the signal polypeptide being specifically cleavable in an intra- or extracellular environment. Finally, ECGF may be produced by direct expression in mature form without the necessity of cleaving away any extraneous polypeptide.

Recombinant host cells refer to cells which have been transformed with vectors constructed using recombinant DNA techniques. As defined herein, ECGF is produced as a consequence of this transformation. ECGF or its fragments produced by such cells are referred to as "recombinant ECGF".

B. Recombinant and Screening Methodology

The procedures below are but some of a wide variety of well established procedures to produce specific reagents useful in the process of this invention. The general procedure for obtaining an mRNA mixture is to obtain a tissue sample or to culture cells producing the desired protein, and to extract the RNA by a process such as that disclosed by Chirgwin, et al., *Biochemistry,* 18:5294 (1979). The mRNA is enriched by poly(A)mRNA containing material by chromatography on oligo (dT) cellulose or poly(U) Sepharose, followed by elution of the poly(A) containing mRNA fraction.

The above poly(A) containing mRNA-enriched fraction is used to synthesize a single-strand complementary cDNA (ss-cDNA) using reverse transcriptase. As a consequence of DNA synthesis, a hairpin loop is formed at the 3' end of the DNA which will initiate second-strand DNA synthesis. Under appropriate conditions, this hairpin loop is used to effect synthesis of the ds-cDNA in the presence of DNA polymerase and deoxyribonucleotide triphosphates.

The resultant ds-cDNA is inserted into the expression vector by any one of many known techniques. In general, methods can be found in Maniatis, et al., supra, and *Methods In Enzymology,* Volumes 65 and 68 (1980); and 100 and 101 (1983). In general, the vector is linearized by at least one restriction endonuclease, which will produce at least two blunt or cohesive ends. The ds-cDNA is ligated with or joined into the vector insertion site.

If prokaryotic cells or other cells which contain substantial cell wall material are employed, the most common method of transformation with the expression vector is calcium chloride pretreatment as described by Cohen, R. N., et al., *Proc. Nat'l. Acad. Sci. USA,* 69:2110 (1972). If Cells without cell wall barriers are used as host cells, transfection is carried out by the calcium phosphate precipitation method described by Graham and Van der Eb, *Virology,* 52:456 (1973). Other methods for introducing DNA into cells such as nuclear injection, viral infection or protoplast fusion may be successfully used. The cells are then cultured on selective media, and proteins for which the expression vector encodes are produced.

Clones containing part or the entire cDNA for ECGF are identified with specific oligonucleotide probes deduced from a partial amino acid sequence determination of ECGF. This method of identification requires that the non-degenerate oligonucleotide probe be designed such that it specifically hybridizes to ECGF ds-cDNA. Clones containing ECGF cDNA sequences are isolated by radioactively labeling the oligonucleotide probe with 32P-ATP, hybridizing the radioactive oligonucleotide probe to the DNA of individual clones of a cDNA library containing ECGF-cDNA, and detection and isolation of the clones which hybridize by autoradiography. Such a cloning system is applicable to the lambda gt11 system described by Young and Davis, supra. Clones containing the entire sequence of ECGF are identified using as probe the cDNA insert of the ECGF recombinants isolated during the initial screening of the recombinant lambda gt11 cDNA library with ECGF-specific oligonucleotides. Nucleotide sequencing techniques are used to determine the sequence of amino acids encoded by the cDNA fragments. This information may be used to determine the identity of the putative ECGF cDNA clones by comparison to the known amino acid sequence of the amino-terminus of bovine ECGF and of a peptide derived by cyanogen bromide cleavage of ECGF.

EXAMPLE

A. Preparation of Total RNA

Total RNA (messenger, ribosomal and transfer) was extracted from fresh two-day old human brain stem essentially as described by Chirgwin, supra, (1979). Cell pellets were homogenized in 5 volumes of a solution containing 4M guanidine thiocyanate, and 25 mM Antifoam A (Sigma Chemical Co., St. Louis, Mo.). The homogenate was centrifuged at 6,000 rpm in a Sorvall GSA rotor for 15 minutes at 10° C. The supernatant fluid was adjusted to pH 5.0 by addition of acetic acid and the RNA precipitated by 0.75 volumes of ethanol at <20° C. for two hours. RNA was collected by centrifugation and dissolved in 7.5M guanidine hydrochloride containing 2 mM sodium citrate and 5 mM dithiothreitol. Following two additional precipitations using 0.5 volumes of ethanol, the residual guanidine hydrochloride was extracted from the precipitate with absolute ethanol. RNA was dissolved in sterile water, insoluble material removed by centrifugation, and the pellets were re-extracted with water. The RNA was adjusted to 0.2M potassium acetate and precipitated by addition of 2.5 volumes of ethanol at −20° C. overnight.

B. Preparation of Poly(A)-containing RNA

The total RNA precipitate, prepared as described above, was dissolved in 20 mM Hepes buffer (pH 7.2) containing 10 mM EDTA and 1% SDS, heated at 65° C. for 10 minutes, then quickly cooled to 25° C. The RNA solution was then diluted with an equal volume of water, and NaCl was added to bring the final concentration to 300 mM NaCl. Samples containing up to 240 A260 units of RNA were chromotagraphed on poly(U)-Sepharose using standard procedures. Poly(A)-containing RNA was eluted with 70% formamide containing 1 mM Hepes buffer (pH 7.2), and 2 mM EDTA. The eluate was adjusted to 0.24M NaCl and the RNA was precipitated by 2.5 volumes of ethanol at −20° C.

C. Construction of cDNA Clones in Lambda gt11

Figure 1:
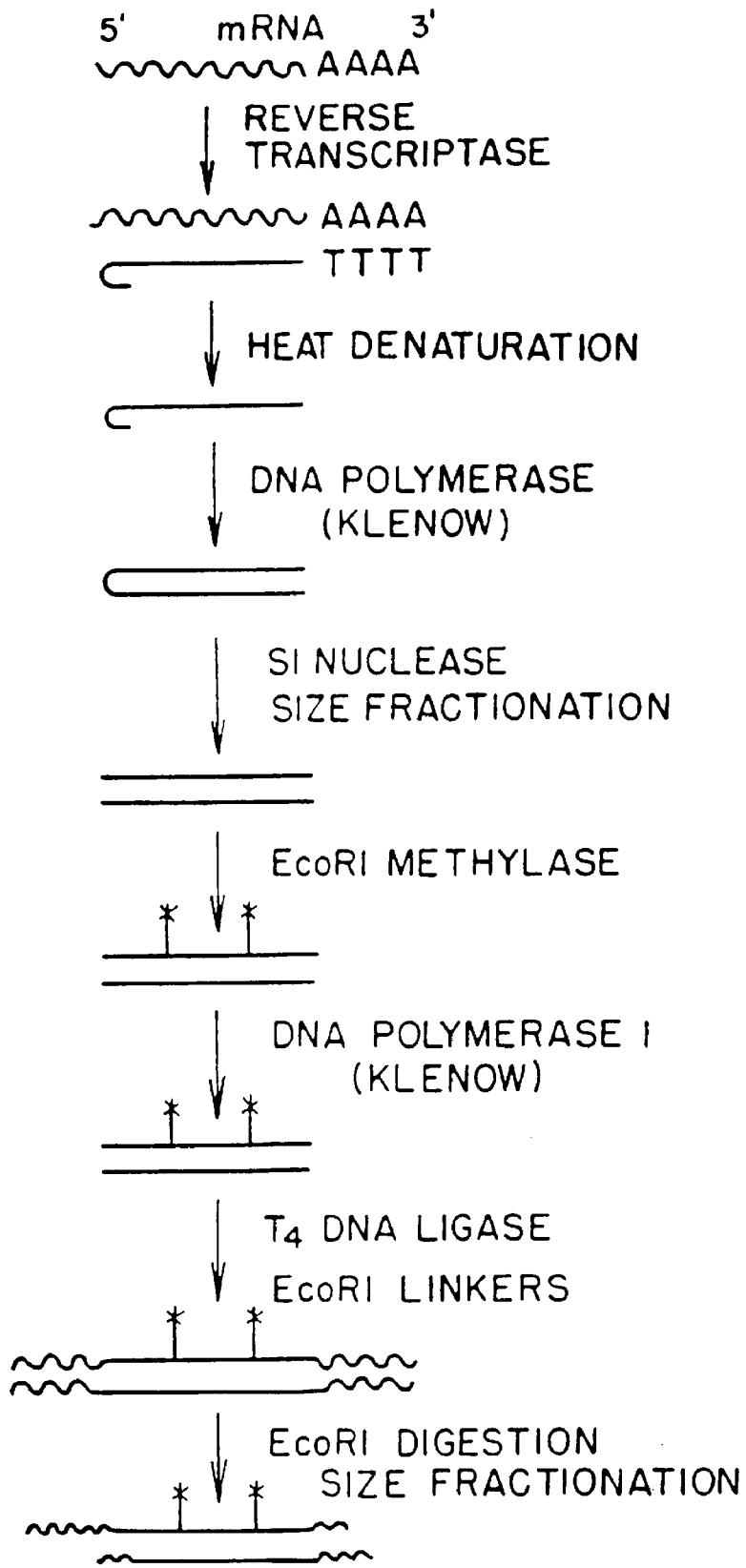
FIG. 1 illustrates a general procedure for enzymatic reactions to produce cDNA clones.

The procedure followed for the enzymatic reaction is shown in FIG. 1. The mRNA (20 μg) was copied into ds-cDNA with reverse transcriptase and DNA polymerase I exactly as described by Buell, et al., supra, and Wilkensen, et al., *J. Biol. Chem.*, 253:2483 (1978). The ds-cDNA was desalted on Sephadex G-50 and the void-volume fractions further purified on an Elutip-D column (Schleicher & Schuell, Keene, N.H.) following the manufacturer's directions. The ds-cDNA was made blunt-ended by incubation with S1 nuclease [Ricca, et al., *J. Biol. Chem.*, 256:10362 (1981)]. The reaction mixture consisted of 0.2M sodium acetate (pH 4.5), 0.4M sodium chloride, 2.5 mM zinc acetate and 0.1 unit of S1 nuclease per ng of ds-cDNA, made to a final reaction volume of 100 μl. The ds-cDNA was incubated to 37° C. for one hour, extracted with phenol:chloroform, and then desalted on a Sephadex G-50 column as described above.

The ds-cDNA was then treated with EcoRI methylase and Klenow fragment of DNA polymerase I using reaction conditions described in Maniatis, et al., *Molecular Cloning*, supra. The cDNA was again desalted on Sephadex G-50 as described above and then ligated to 0.5 μg of phosphorylated EcoRI linkers using T4 DNA ligase (Maniatis, et al., supra). The mixture was cleaved with EcoRI and fractionated on an 8% acrylamide gel in Tris-borate buffer (Maniatis, et al., supra). DNA with a size greater than 1 kilobase was eluted from the gel and recovered by binding to an Elutip-D column, eluted with 1M NaCl and then collected by ethanol precipitation.

Figure 2:
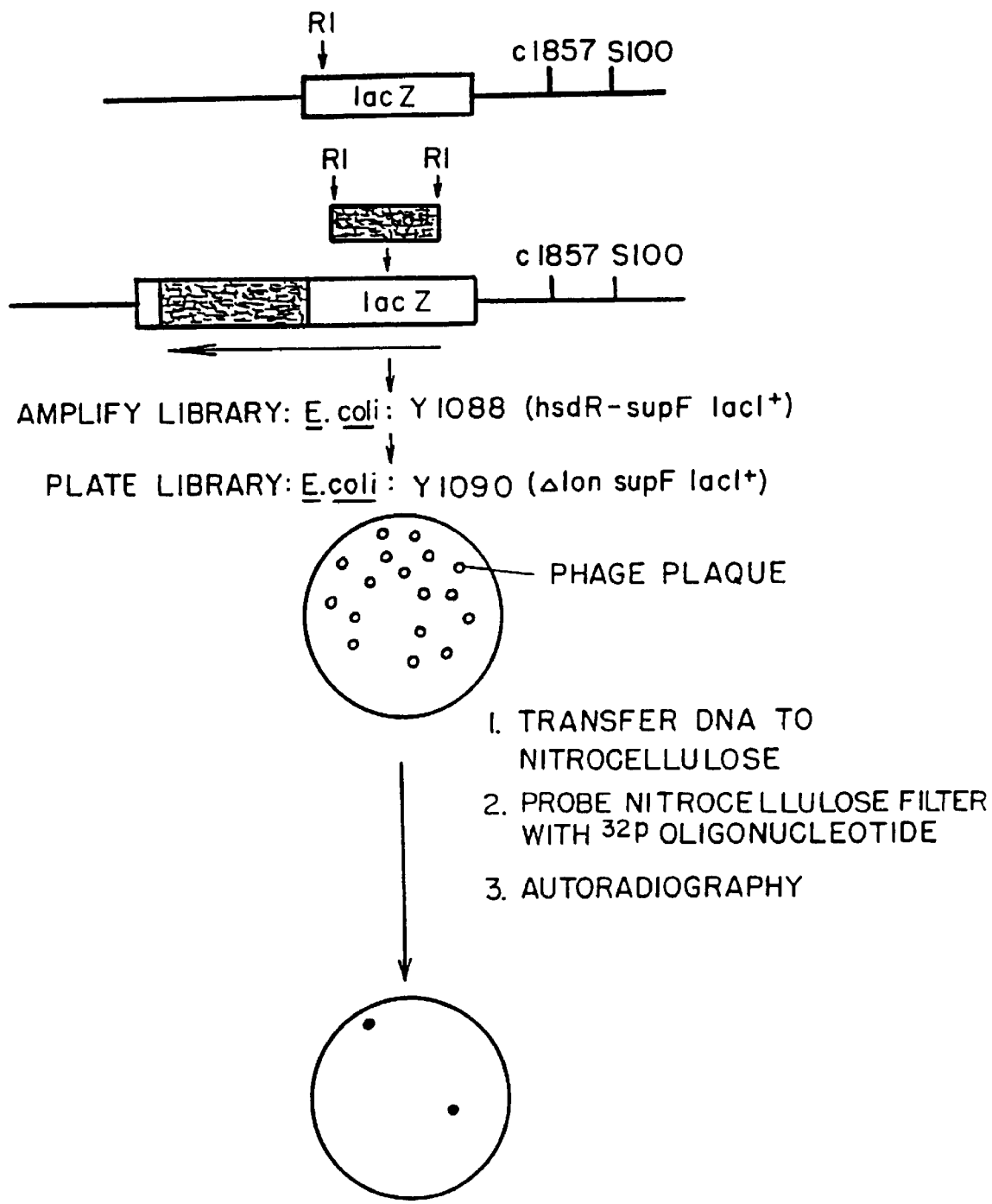
FIG. 2 illustrates the production of a library containing DNA fragments inserted into lambda gtll.

As shown in FIG. 2, the DNA fragments were then inserted into EcoRI cleaved and phosphatase-treated lambda gt11, using T4 DNA ligase. A library of 5.7×106 phage was produced, of which approximately 65% were recombinant phage. The library was amplified by producing plate stocks at 42° C. on *E. coli* Y1088 [supE supF met:B trpR hsdR− hsdM+ tonA21 scrA lacU169 (proC::Tn5) (pMC9)]. Amplification procedures are described in Maniatis, et al., supra. Important features of this strain, described by Young and Davis, supra, include (1) supF (required suppression of the phage amber mutation in the S gene), (2) hsdR− hsdM+ (necessary to prevent restriction of foreign DNA prior to host modification), and (3) lacU169 (proC::Tn5), and (4) (pMC9) (a lac I-bearing pBR322 derivative which represses, in the absence of an inducer, the expression of foreign genes that may be detrimental to phage and/or cell growth).

D. Identification of Clones Containing ECGF Sequence

To screen the library for recombinant phage containing ECGF cDNA, 1.5×106 phage were plated on a lawn of *E. coli* Y1090 [delta lacU169 proA delta lon araD139 strA supF (trpC22::TnIO) (pMC9)] and incubated at 42° C. for 6 hours. After the plates were refrigerated overnight, a nitrocellulose filter was overlaid on the plates. The position of the filter was marked with a needle. The filter removed after one minute and left to dry at room temperature. From each plate, a duplicate filter was prepared exactly as described, except that the filter was left in contact with the plate for 5 minutes. All filters were then prepared for hybridization, as described in Maniatis, et al., supra. This involved DNA denaturation in 0.5M NaOH, 1.5M NaCl, neutralization in 1M Tris-HCl, pH 7.5, 1.5M NaCl, and heating of the filters for 2 hours at 80° C. in vacuo.

To screen the human brain stem cDNA library for clones containing ECGF inserts, a specific oligonucleotide was designed. This oligonucleotide was based upon a partial amino acid sequence analysis of the amino terminus of ECGF. As shown in FIG. 3, lines a & b, bovine ECGF is isolated as two species, designated alpha and beta ECGF, which differ only in the amino acids found at the respective amino termini. As shown in FIG. 3, lines a & b, beta-ECGF is a slightly larger species than alpha-ECGF. The exact amino acid sequence at the amino terminus of beta-ECGF is undetermined, however, a sequence derived from fast atom bombardment mass spectral analysis and the amino acid composition of the amino terminal tryptic peptide of bovine beta-ECGF is shown. The amino terminal blocking group appears to be acetyl. If intact beta-ECGF is cleaved by trypsin, a second amino amino acid sequence found in beta but not alpha ACGF starting with PheAsnLeu . . . is determined. This sequence is also found at the amino terminus of acidic fibroblast growth factor [Thomas, K. A.

et al., Prac. Natl. Acad. Sci., 82:6409–6413 (1985)]. The amino terminus of alpha-ECGF is AsnTyrLys . . . (FIG. 3, line a) and is the equivalent of beta-ECGF minus an amino terminal extension. In FIG. 3, lines c and d set forth for comparison the amino acid sequence of cyanogen bromide-cleaved bovine alpha and beta ECGF, respectively.

For oligonucleotide design, the amino acid sequence IleLeuProAspGlyThrValAspGllyThrLys, corresponding to alpha-ECGF amino acids 19–29 inclusive, was chosen. Rather then design a mixture of oligonucleotides covering all of the possible coding sequences (owing to the degeneracy of the genetic code), a long unique oligonucleotide was designed. Such oligonucleotide probes have been previously shown to be successful probes in screening complex cDNA [Jaye, et al., *Nucleic Acids Research* 11:2325–2335, (1983)] and genomic [Gitschier, et al., *Nature,* 312:326–330 (1984)] libraries. Three criteria were used in designing the ECGF probe: (1) The dinucleotide CG was avoided. This strategy was based upon the observed underrepresentation of the CG dinucleotide in eukaryotic DNA [Josse, et al., *J. Biol. Chem.* 236:864–875, (1961)]; (2) preferred codon utilization data was used wherever possible. A recent and comprehensive analysis of human codon utilization was found in Lathe, *J. Biol.* 183:1–12 (1985); and (3) wherever the strategies of CG dinucleotide and preferred codon utilization were uninformative, unusual base pairing was allowed. This strategy was based upon the natural occurrence of G:T, I:T, I:A and I:C base pairs which occur in the interaction between tRNA anticodons and mRNA codons [Crick, *J. Mol. Biol.* 19:548–555, (1966)]. A diagram of usual and unusual base pairs is shown in FIG. 4. Use of I (Inosine) in a hybridization probe was first demonstrated, in a model experiment, by Ohtsuka, et al., *J. Biol. Chem.* 260:2605–2608 (1985). The overall strategy and choice made in the design of the oligonucleotide used to screen the human brain stem cDNA library for ECGE is shown in FIG. 5. In addition, two other oligonucleotides, designed with the same strategy, were constructed.

Approximately 30 pmole of the oligonucleotide shown in FIG. 5 were radioactively labeled by incubation with 32P-gamma-ATP and T4 polynucleotide kinase, essentially as described by Maniatis, et a:., supra. Nitrocellulose filters, prepared as described above, were prehybridized at 42° C. in 6X SSPE (1X SSPE=0.18M NaCl, 0.01M NaHP04 pH 7.2, 0.001M EDTA), 2X Denhardt's (1X Denhardt's–0.02% each Ficoll, polyvinylpyrrolidone, bovine serum albumin), 5% dextran sulfate, and 100 mu g/ml denatured salmon sperm DNA. The 32P-labeled oligonucleotide was added following four hours of prehybridization, and hybridization continued overnight at 42° C. Unhybridized probe was removed by sequential washing at 37° C. in 2X SSPE, 0.1% SDS.

From 1.5x106 plaques screened, 2 plaques gave positive autoradiographic signals after overnight exposure. These clones were purified to homogeneity by repeated cycles of purification using the above oligonucleotide as hybridization probe.

The two clones that were isolated, ECGF clones 1 and 29, were analyzed in further detail. Upon digestion with EcoRI, clone 1 and 29 revealed cDNA inserts of 2.2 and 0.3 Kb, respectively. Nick translation of cloned cDNA and its subsequent use as a radiolabeled probe in Southern blot analysis (Maniatis, et al., supra) revealed that clones 1 and 29 were related and overlapping clones. The overlapping nature of these two clones is shown in FIG. 6.

Clones 1 and 29 were analyzed in further detail as follows: An additional two oligonucleotides were designed, based upon the amino acid sequence of bovine ECGF. These oligonucleotides were designed based upon the same considerations as those used in the design of the oligonucleotide used to isolate clones 1 and 29. These oligonucleotides (ECGF oligonucleotides II and III) are shown in FIG. 7. These two oligonucleotides as well as oligo(dT)18 were radioactively labeled in a kination reaction as described above and used as hybridization probes in Southern blotting experiments. The results of these experiments showed that the 0.3 Kb cDNA insert of clone 29 hybridized to ECGF oligonucleotides I and 11 but not to ECGF oligonucleotide III or oligo (dT)18; the 2.2 Kb cDNA insert of clone 1 hybridized to oligonucleotide I, II, III as well as oligo(dT) 18. These data and subsequent nucleotide sequence determination of clones 1 and 29 showed that the 3' end of clone 1 ends with a poly(A) tail. Hybridization of clone 1 to ECGF oligonucleotide III, which is based on a cyanogen bromide cleavage product of bovine ECGF, as well as to oligo (dT)18, strongly suggested that this clone contains the rest of the coding sequence for both alpha and beta ECGFs as well as a large (greater than 1 Kb) 3' flanking sequence.

The cDNA inserts from clones 1 and 29 were isolated, subcloned into M13mpl8, and the ECGF-encoding open reading frame and flanking regions sequenced by the chain termination method [Sanger et al., *Proc. Natl. Acad. Sci. USA* 74:5463–5467 (1977)]. The nucleotide sequence of these clones and the amino acid sequence deduced from the nucleic acid sequence is shown in FIG. 8. Examination of the nucleotide sequence reveals an open reading frame of 465 nucleotides encoding human ECGF. The 155 amino acids of human ECGF were found to be flanked by translation stop codons. The $NH_2$-terminal amino acid of human beta ECGF deduced from the cDNA sequence is methionine, which most likely serves as the translation initiation residue. These data, together with the relatively non-hydrophobic nature of the first 15–20 amino terminal residues, strongly suggest that human beta ECGF is synthesized without a NH2-terminal signal peptide. A comparison of FIGS. 3 and 8 shows that the amino terminal amino acid sequence of trypsin-cleaved bovine beta ECGF as well as that of bovine alpha ECGF are nearly identical to the amino acid sequence predicted from the nucleotide sequence of lambda ECGF clones 1 and 29. An overall homology between the two species of over 95% is observed.

Northern blot analysis (Maniatis, et al, supra) reveals that ECGF mRNA is a single molecular species which comigrates with 28S rRNA (FIG. 9). Considering the variation in the estimated size of 28S rRNA, the approximate size of ECGF mRNA is 4.8±1.4 Kb. All of the sequence encoding the mature forms of both alpha and beta ECGF is encoded within ECGF Clones 1 and 29, which together encompasses approximately 2.3 Kb. Thus, these data demonstrate that the region 5' and flanking the ECGF-encoding sequences, is very large (approximately 2.5±1.4 Kb).

cDNA inserts from Clone 1 and Clone 29 were excised by digestion with EcoRI and subcloned in pUC8 at the EcoRI site. The plasmid formed from Clone 1 was designated pDH15 and the plasmid formed from Clone 29 was designated pDH14.

Clone I was improved by inserting it into a vector allowing more efficient expression of α-ECGF. This vector is pMJ26 and places this gene under a high-effeciency tac promoter as described in FIG. 10 and as done as follows. A double-stranded Bam HI cohesive 66-mer oligonucleotide encoding residues 1-l9 of α-ECGF, preceded by initiator methionine, was synthesized by the phosphoramoridite method and purified. The oligonucleotide was ligated between the Bam HI sites of pDHI5 creating pMJ25. In order to introduce appropriate regulatory sequences, the α-ECGF-encoding open reading frame was excised from pMJ25 by digestion with Eco RI and Hinc II and cloned between the Eco RI and Sma I sites of pKK223-3 (PL Biochemicals). The recombinant plasmid, pMJ26, was introduced into the lac-i-Q bearing *E. coli* strain, JMTO3, to evaluate expression of α-ECGF.

In pMJ26, expression of α-ECGF, under control of the hybrid tac promoter, is inducible with IPTG. To measure α-ECGF production, logarithmically grown bacterial cultures containing pMJ26 at $A_{550}$ of 0.2 were induced with 1 mM IPTG and grown for 2–4 hours at 37° C. prior to harvesting, lysis and growth factor isolation. Control extracts were prepared from uninduced cultures of pMJ26 and from induced and uninduced bacterial cultures not containing the ECGF gene. All extracts were fractionated by SDS-PAGE, and the protein visualized by staining with Coomassie brilliant blue. As shown in FIG. 11, lane b, a prominant band at approximately 16 kd is observed in induced cultures of pMJ26. The band is observed at low levels when pMJ26 is not induced, lane a, (this reflects the leakiness of the tac promoter) and, as expected, is absent in either induced or control cultures of bacterial which do not contain the α-ECGF gene.

The ability to induce a polypeptide of the expected size, specifically, in bacteria containing the α-ECGF gene, suggests the successful expression of the human α-ECGF. The protein was purified by a two-step procedure involving heparin-Sepharose column chromatography followed by reversed phase HPLC analysis. (Burgess, W. H., Mehiman, T., Friesel, R., Johnson, W. V., and Maciag, T. (1985) J. Biol. Chem. 260, 11389–11392.) Protein evaluated by this method is essentially pure and amino terminal and amino acid sequence analyses demonstrate the predicted amino acid sequence of α-ECGF of MNYKKPKLLYCSNG. Data suggests (FIG. 11) pMJ26 can express α-ECGF to approximately 10% of the total protein of *E. coli* and remain soluble in this bacteria allowing his rapid two-step purification. To establish that this protein is biologically active, it was compared to bovine ECGF in several established assays.

In these assays, the functional activities of recombinant human α-ECGF were examined. The success of the heparin-Sepharose affinity based purification demonstrates that recombinant α-ECGF (FIG. 12B). Together these data indicate that the heparin binding properties of the recombinant material are similar to those of bovine brain-derived ECGF.

The results of cellular receptor assays (Friesel, R., Burgess, W. H., Mehlman, T., and Maciag, T. (1986) J. Biol. Chem. 261, 7581–7584; Schreiber, A. B., Kenney, J., Kawalski, J., Firesel, R., Mehlman, T., and Maciag, T. (1985) Proc. Nat'l. Acad. Sci. U.S.A. 82, 6138–6143) indicate that the receptor binding activity of recombinant human α-ECGF also is similar to bovine brain-derived ECGF. Radioiodinated bovine α-ECGF was incubated with murine endothelial cells at 4° C. in the presence of increasing quantities of either bovine or recombinant human α-ECGF. After 30 minutes, the cell monolayer was washed and the cell-associated radioactivity determined. As shown in FIG. 12a, the displacement curves for both bovine and human recombinant α-ECGF are very similar. The receptor-binding activity of the recombinant protein was abolished after reduction and alkylation (FIG. 12A).

The mitogenic activities of native and recombinant α-ECGR were in two separate assays. In the first assay DNA synthesis was monitored by incorporation of $[^3H]$-thymidine into TCA-precipitable material as a function of increasing quantities of α-ECGF (FIG. 12B). The second assay compared the stimulation of both preparations of ECGF upon the proliferation of HUVEC (FIG. 12C). In the $[^3H]$-thymidine incorporation assay (FIG. 12B), the maximal response observed with bovine brain-derived ECGF, while the dose for each which gave half-maximal stimulation was similar ($EC_{50}$ of bovine α-ECGF=1.75 ng/ml; $EC_{50}$ of recombinant human α-ECGF=0.5 ng/ml). In the HUVEC assay (FIG. 12C), the maximal stimulation observed with bovine and recombinant human ECGF were similar, as were the concentrations giving half-maximal stimulation ($EC_{50}$ of bovine α-ECGF=0.6 ng/ml; $EC_{50}$ of recombinant human α-ECGF= 0.45 ng/ml). Heparin (5 U/ml) was found to potentiate the mitogenic effect of both bovine and recombinant human α-ECGF 5–10 fold. These date demonstrate that human recombinant α-ECGF has biological properties similar to bovine ECGF.

Thus, this example describes experimental procedures which provide human endothelial cell growth factor essentially free of other proteins of human origin.

UTILITY

ECGF has utility in the growth and amplification of endothelial cells in culture. Currently, ECGF for cell culture use is extracted from bovine brain by the protocol of Maciag, et al., [*Proc. Natl. Acad. Sci.,* 76:11, 5674–5678 (1978)]. This crude bovine ECGF is mitogenic for human umbilical vein endothelial cells [Maciag, et al., *J. Biol. Chem.* 257:5333–5336 (1982)] and endothelial cells from other species. Utilization of heparin with ECGF and fibronectin matrix permits the establishment of stable endothelial cell clones. The recommended concentration of this crude bovine ECGF for use a mitogen in vitro is 150 micrograms per milliliter of growth medium.

Recombinant DNA-derived human ECGF has utility, therefore, as an improved substitute for crude bovine ECGF in the in vitro culturing of human endothelial cells and other mesenchymal cells for research use. The activity of human ECGF is expected to be the same as or better than bovine ECGF in the potentiation of endothelial cell growth due to the high degree of homology in the amino acid sequences of both proteins. The expected effective dose range for potentiating cell division and growth in vitro is 5–10 ng of purified ECGF per milliliter of culture medium. Production of the ECGF via recombinant-DNA technologies as outlined in this patent application and subsequent purification as described by Burgess, et al., [*J. Biol. Chem.* 260:11389–11392 (1985)] will provide large quantities of a pure product of human origin (heretofore unavailable in any quantity or purity) with which to develop models of human homeostatis and angiogenesis.

Recombinant DNA-derived human ECGF also has utility in the potentiation of cell growth on a prosthetic device, rather than a tissue culture flask or bottle. This device may or may not be coated with other molecules which would facilitate the attachment of endothelial cells to the device. These facilitating molecules may include extracellular matrix components, human serum albumin, or inert organic molecules.

The extracellular matrix is comprised of several fibrous proteins imbedded in a gel comprised of glycosaminoglycan polysaccharides. The glycosaminoglycans are usually linked to a protein core to form proteoglycans (Alberts et al. in "Molecular Biology of the Cell" Garland Publishing, Inc. (1983) pp. 692–715; the contents of which are incorporated herein by reference). Among the protein components of the extracellular matrix are collagen, elastin, laminin and fibronectin. Collagen has a stiff, triple-stranded helical structure and exists in at least 5 major forms (Types 1-V). Types I–III are predominent in connective tissue, while Type IV is found in the basal lamina. Type V is widespread in different tissues, although in relatively small amounts. Fibronectin is a glycoprotein that promotes cell adhesion and exists as large aggregates in the extracellular space. Laminin is a component of the basal lamina.

Glycosaminoglycans are long, unbranched polysaccharide chains composed of repeating disaccharide units. They are highly negatively charged and capable of attracting large amounts of water, thereby forming hydrated gels even at low concentrations. The glycosaminoglycans include hyaluronic acid, chondroitin 4-sulfate, chondroitin 6-sulfate, dermatan sulfate, heparan sulfate, heparin and keratan sulfate. Hyaluronic acid is the only glycosaminoglycan that does not form a proteoglycan structure.

For potentiation of cell growth, such as on the surface of a prosthetic device, endothelial cells would be cultured in the presence of effective doses of ECGF, and optionally one or more extracellular matrix components. This device would then provide a non-thrombogenic surface on the prosthetic device, thus reducing the risk of potentially life-threatening thrombogenic events subsequent to implantation of the prosthetic device.

ECGF has utility in diagnostic applications. Schreiber, et al., [*Proc. Natl. Acad. Sci.* 82:6138 (1985)] developed a double antibody immunoassay for bovine ECGF. In this assay, 96-well polyvinyl chloride plates were coated with rabbit anti-ECGF and the remaining binding sites subsequently blocked with 10% normal rabbit serum. Samples of ECGF were then added to the wells and incubated. After washing, murine monoclonal anti-ECGF was added. After incubation and several washes, rabbit anti-mouse IgG coupled with peroxidase was added. The reaction product was quantitated spectrophotometrically after conversion of O-phenylenediamine in the presence of hydrogen peroxide. A similarly constructed immunoassay may be useful for monitoring human ECGF levels in disease states affecting endothelial cell growth. Purified recombinant-DNA derived ECGF would be useful as a standard reagent in quantifying unknown ECGF samples.

ECGF also may have potential in the treatment of damaged or in the regeneration of blood vessels and other endothelial cell-lined structures.

It should be appreciated that the present invention is not to be construed as being limited by the illustrative embodiment. It is possible to produce still other embodiment. It is possible to produce still other embodiments without departing from the inventive concepts herein disclosed. Such embodiments are within the ability of those skilled in the art.

Deposit of Strains Useful in Practicing the Invention

Biologically pure cultures of strains for practicing this invention are available at the offices of Rorer Biotechnology Inc.

Access to said cultures will be available during pendency of the patent application to one determined by the Commissioner to be entitled thereto under 37 C.F.R. Section 1.14 and 35 U.S.C. Section 122.

At a date prior to issuance a deposit of biologically pure cultures of the strains within the allowed claims will be made with the American Type Culture Collection, 12301 Parklawn Drive, Rockville, Md., the accession number assigned after successful viability testing will be indicated by amendment below, and the requisite fees will be paid.

All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture (s) of the same taxonomic description.

| Strain/Plasmid | ATCC No. | Deposit Date |
|---|---|---|
| pDH 15 | 53366 | November 25, 1985 |
| pDH 14 | 53365 | November 25, 1985 |
| pMJ 26 | 67857 | November 23, 1988 |

What is claimed is:

1. A composition comprising a human endothelial cell growth factor in an amount effective to promote wound healing and an acceptable carrier, wherein said endothelial cell growth factor either has the amino acid sequence of α-endothelial cell growth factor (NYKKPKLLYCSNGGHFLRILP-
   DGTVDGTRDRSDQHIQLQLSAESVGEVYI KSTETGQY-
   LAMDTDGLLYGSQTPNEECLFLERLEEN-
   HYNTYISKKHAEKN
   WFVGLKKNGSCKRGPRTHYGQKAILFLPLPVSSD)

or comprises the amino acid sequence of β-endothelial cell growth factor (AEGEITTFTALTEKFNLPPGNYKKPKL-
   LYCSNGGHFLRILPDGTVDGTRDR SDQHIQLQLSAESV-
   GEVYIKSTETGQYLAMDTDGLLYGSQTPNEECLFLER
   LEENHYNTYISKKHAEKNWFVGLKKNG-
   SCKRGPRTHYGQKAILFLPLPVS SD).

2. A composition according to claim 1, further comprising heparin.

3. A composition comprising purified and isolated biologically active human recombinant β-endothelial cell growth factor, an acceptable carrier and an extracellular matrix component selected from the group consisting of an extracellular matrix protein and a glycosaminoglycan, wherein said β-endothelial cell growth factor comprises the amino acid sequence AEGEITTFTALTEKFNLPPGNYKKPKLLYCSNGGHFLR ILP-
   DGTVDGTRDRSDQHIQLQLSAESVGEVYIKSTETG
   QYLAMDTDGLLYGSQTPNEECLFLERLEENHYNTYIS
   KKHAEKNWFVGLKKNGSCKRGPRTHYGQKAILFLPL
   PVSSD.

4. A composition according to claim 3, wherein the extracellular matrix protein is fibronectin, laminin or a collagen.

5. A composition according to claim 3, wherein the glycosaminoglycan is heparin.

6. A composition comprising purified and isolated biologically active human recombinant β-endothelial cell growth factor, an acceptable carrier and human serum albumin, wherein said β-endothelial cell growth factor comprises the amino acid sequence AEGEITTFTALTEKFNLPPGNYKKPKLLYCSNGGHFLR ILP-
   DGTVDGTRDRSDQHIQLQLSAESVGEVYIKSTETG
   QYLAMDTDGLLYGSQTPNEECLFLERLEENHYNTYIS
   KKHAEKNWFVGLKKNGSCKRGPRTHYGQKAILFLPL
   PVSSD.

7. A composition comprising purified and isolated biologically active human recombinant α-endothelial cell growth factor, an acceptable carrier and an extracellular matrix component selected from the group consisting of an extracellular matrix protein and a glycosaminoglycan, wherein said α-endothelial cell growth factor has the amino acid sequence NYKKPKLLYCSNGGHFLRILPDGTVDGTRDRSDQHI QLQLSAESVGEVYIKSTETGQYLAMDTDGLLYGSQ TPNEECLFLERLEENHYNTYISKKHAEKNWFVGLK KNGSCKRGPRTHYGQKAILFLPLPVSSD.

8. A composition according to claim 7, wherein the extracellular matrix protein is fibronectin, laminin or a collagen.

9. A composition according to claim 7, wherein the glycosaminoglycan is heparin.

10. A composition comprising purified and isolated biologically active human recombinant α-endothelial cell growth factor, an acceptable carrier and human serum albumin, wherein said α-endothelial cell growth factor has the amino acid sequence NYKKPKLLYCSNGGHFLRILPDGTVDGTRDRSDQHI QLQLSAESVGEVYIKSTETGQYLAMDTDGLLYGSQ TPNEECLFLERLEENHYNTYISKKHAEKNWFVGLK KNGSCKRGPRTHYGQKAILFLPLPVSSD.

* * * * *